United States Patent
Wang et al.

(10) Patent No.: US 6,169,407 B1
(45) Date of Patent: Jan. 2, 2001

(54) WATER CONTENT METERING APPARATUS

(75) Inventors: Xin Xin Wang, Naperville; Thaddeus A. Niemiro, Lisle; Thomas W. Orzechowski, Orland Park; Shem-Mong Chou, Westmont, all of IL (US)

(73) Assignee: Goss Graphics Systems, Westmont, IL (US)

( * ) Notice: Under 35 U.S.C. 154(b), the term of this patent shall be extended for 0 days.

(21) Appl. No.: 09/050,880

(22) Filed: Mar. 30, 1998

Related U.S. Application Data (60) Provisional application No. 60/057,442, filed on Sep. 2, 1997.

(51) Int. Cl.$^7$ .................................................. G01R 27/26
(52) U.S. Cl. .......................... 324/690; 324/664; 324/667
(58) Field of Search ..................... 324/661, 667, 324/601, 664, 686–610; 73/61.61, 61.43; 78/69

(56) References Cited

U.S. PATENT DOCUMENTS

| | | | |
|---|---|---|---|
| 1,960,168 | 5/1934 | Schoenberg | 324/661 |
| 2,544,529 | 3/1951 | Fieldem | 324/667 |
| 3,025,465 | 3/1962 | Breen | 324/689 |
| 3,696,299 | 10/1972 | Pullman et al. | 324/673 |
| 3,739,266 | 6/1973 | Neitzel et al. | 324/667 |
| 3,825,682 * | 7/1974 | Phillips | 178/69 |
| 4,048,844 | 9/1977 | Dunikowski et al. | 73/32 R |
| 4,112,744 | 9/1978 | Tassano . | |
| 4,130,796 | 12/1978 | Shum | 324/601 |
| 4,399,404 | 8/1983 | Resh | 324/689 |
| 4,429,273 | 1/1984 | Mazzagatti | 324/664 |
| 4,468,611 * | 8/1984 | Tward | 324/61 |
| 4,559,493 | 12/1985 | Goldberg et al. | 324/681 |
| 4,658,207 | 4/1987 | Scribano et al. | 324/669 |
| 4,916,940 | 4/1990 | Mougne | 73/61.43 |
| 5,125,265 | 6/1992 | O'Connell et al. | 73/61.41 |
| 5,927,200 * | 7/1999 | Shem-Mong | 101/364 |

FOREIGN PATENT DOCUMENTS

| | | |
|---|---|---|
| 24 12 165 | 9/1975 | (DE) . |
| 0 341 675 | 11/1989 | (EP) . |
| 0 590 503 | 4/1994 | (EP) . |
| 2 610 724 | 2/1987 | (FR) . |

OTHER PUBLICATIONS

Ira B. Goldberg, Mark Cher, Thomas A. Fadner and Bruce E. Blom, Physico–Chemical Measurements Relating To The Structure of Ink–Fountain Solution Mixtures, Technical Association of The Graphic Arts, Proceedings of 1986, pp. 14–36. (No Month Available).

PCT *International Search Report,* Dated Apr. 12, 1998. PCT Application Serial No. PCT/US98/17719. International Filing Date Aug. 26, 1998.

\* cited by examiner

*Primary Examiner*—Safet Metjahic
*Assistant Examiner*—James C Kerveros
(74) *Attorney, Agent, or Firm*—Marshall, O'Toole, Gerstein, Murray & Borun (57) ABSTRACT

A water metering apparatus for measuring water concentrations in a water-ink emulsion used in a printing press is provided. The apparatus develops a substantially linear output for water concentrations ranging from 0% to approximately 50% without employing a logarithmic amplifier. In addition, an improved sensor for use in the water metering apparatus is provided.

23 Claims, 8 Drawing Sheets

WATER CONTENT METERING APPARATUS

RELATED APPLICATIONS

This application claims priority from U.S. Provisional Patent Application Ser. No. 60/057,442, which was filed on Sep. 2, 1997.

FIELD OF THE INVENTION

The present invention relates generally to printing presses and, more particularly, to a water content metering apparatus for monitoring the concentration of water in a water-ink emulsion in a printing press.

BACKGROUND OF THE INVENTION

Lithographic printing presses typically involve two basic materials: ink and dampening solution. The dampening solution usually comprises water with small amounts of additives to enhance water wetting of the nonimage area of the printing plate. Conventionally, ink and dampening solution are supplied as two separate streams.

To simplify the printing press and reduce costs, some single fluid printing presses use a premixed ink and water (or dampening solution) emulsion. For economical operation, the water-ink emulsion must be scraped off the ink train and re-circulated back to the system, since only a fraction of the emulsion is consumed by the printing process at any given time. The scraped emulsion usually contains about 10–20% less water than the original emulsion does. In order to obtain the best printing results, the emulsion must maintain a proper water concentration, which is usually between 30–50% depending upon the ink formulation. In some instances this can be done by mixing a proper proportion of fresh ink and water at the start-up. However, over a period of time as the printing progresses, the proportion of ink and water changes in the re-circulated emulsion. In the case of a continuous application of new emulsion during the printing process, it is often necessary to measure the water concentration of the emulsion on a continuous, real-time basis.

Meters are known which measure the dielectric constant of an emulsion or mixture to determine the moisture content of materials or the density of the emulsion. Some of these prior art meters use a Wheatstone bridge-type circuit to measure dielectric properties (e.g., U.S. Pat. No. 3,696,299). Other prior art meters use two oscillators to obtain a frequency differential which is related to the dielectric properties of the material being tested (e.g., U.S. Pat. No. 4,048,844). Still other prior art meters use an oscillator with peak detectors (e.g., U.S. Pat. No. 4,399,404) or a logic circuit (e.g., U.S. Pat. No. 4,130,796). U.S. Pat. No. 4,559,493 discloses another prior art meter for measuring the concentration of water in a water-ink emulsion. Although the '493 Patent indicates that a logarithmic amplifier may be excluded for concentrations of water in the 0–20% range, most presses employ water-ink emulsions having water concentrations in the 20–50% range and, thus, in the preferred embodiment described in the '493 Patent, a logarithmic amplifier is employed to linearize the output of the sensor.

In addition to requiring logarithmic amplifiers over much of their operating range, prior art meters have suffered from other disadvantages. For example, some prior art meters have been constructed to include capacitive sensors employing electrodes or plates which deform or move under pressure. Such deformation or movement has resulted in outputs which vary in response to flow rates thereby causing inaccuracies in measurements of the subject variable, namely, water concentration.

The outputs of prior art capacitive sensors have also been effected by the distribution of the components within the measured emulsion. For example, water-ink emulsions having precisely the same components will often have different dielectric constants if those components are distributed differently within the emulsion. As an extreme instance, a water-ink emulsion having a uniform distribution or consistent blend will have a different dielectric constant than a water-ink emulsion stratified into water and ink levels even if the two emulsions have precisely the same concentration of ink and water. This problem is explained in the context of oil and water mixtures in U.S. Pat. No. 4,916,490 to Mougne.

Other disadvantages present in the prior art include susceptibility to stray electromagnetic fields which can interfere with accurate measurements.

SUMMARY OF THE INVENTION

The present invention overcomes the drawbacks associated with the prior art by providing an improved water metering apparatus comprising an improved sensor which produces a substantially linear output for a wide range of water concentrations in a consistent water-ink emulsion without employing a logarithmic amplifier.

In accordance with one aspect of the invention, a water metering apparatus comprising a capacitive sensor coupled to an oscillator acting as a multi-vibrator is provided. The measured emulsion is passed between the opposed plates of the capacitive sensor such that the capacitance of the sensor changes to reflect the water content of the emulsion. The output frequency of the oscillator varies with the capacitance of the sensor. The output frequency of the oscillator is converted by a water concentration converter to a signal representative of the water concentration of the measured emulsion. The water concentration converter develops the water concentration signal in accordance with a substantially linear mapping function having a negative slope wherein, as the water concentration increases, the voltage output by the frequency to voltage converter decreases.

In accordance with a further significant aspect of the invention, a water metering apparatus of the foregoing type is provided wherein the mapping function is substantially linear for water concentrations in the 0–50% range.

DESCRIPTION OF THE PREFERRED EMBODIMENTS

Figure 1:
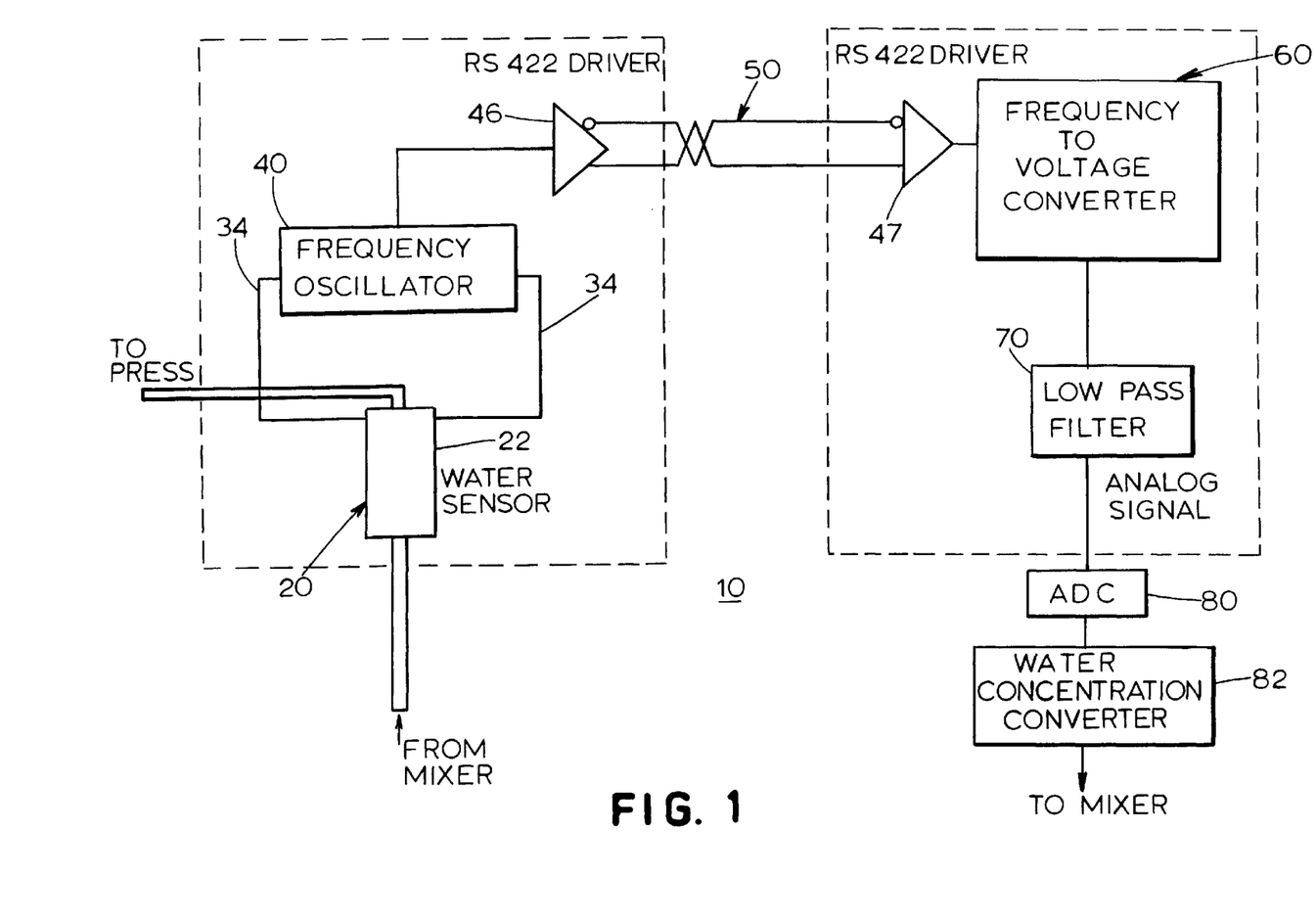
FIG. 1 is a schematic illustration of a water metering apparatus constructed in accordance with the teachings of the instant invention.

A water metering apparatus 10 constructed in accordance with the teachings of the instant invention is shown generally in FIG. 1. The water metering apparatus is particularly well adapted for measuring the water concentration of a water-ink emulsion used by a printing press. However, those skilled in the art will appreciate that the inventive apparatus 10 is not limited to use with a printing press or to use with a specific type of emulsion. Similarly, persons of ordinary skill in the art will readily appreciate that, although the disclosed apparatus 10 is well suited for use with lithographic presses, it is not limited to use with any particular type of press. On the contrary, the inventive apparatus may be employed in any application which could benefit from its characteristics without departing from the scope or the spirit of the invention.

The disclosed apparatus is preferably employed with substantially uniformly blended emulsions to avoid some of the problems associated with prior art devices. A mechanism for producing a substantially uniformly blended emulsion is discussed below. As used herein, the terms "uniformly blended emulsion", "consistently blended emulsion", "uniform emulsion"and/or "consistent emulsion", refer to an emulsion wherein the component parts are, on average, uniformly blended throughout the mixture.

For the purpose of sensing the water concentration present in a monitored emulsion, the metering apparatus 10 is provided with a water sensor 20. As shown in FIG. 1, the water sensor 20 is preferably capacitive in nature and is located to receive a flow of the monitored emulsion from a mixer or the like. As persons of ordinary skill in the art will readily appreciate, the flow need not comprise all of the emulsion being transferred from the mixer to the press. Rather, the flow need only comprise a sample or portion of the emulsion in the system, and that sample could be optionally returned to the system without being sent to the press, without departing from the scope of the invention. Further, while the sensor 20 is preferably located upstream of the press, those skilled in the art will readily appreciate that other locations might likewise be appropriate. For example, in the case of a re-circulating emulsion, the sensor 20 could be disposed downstream of the press without departing from the scope of the invention.

In any event, the emulsion is preferably passed between two opposing plates 22 of the capacitive sensor 20. As capacitance is directly dependent upon the dielectric constant of the material between the plates of the subject capacitor, changing the dielectric material between the plates 22 of the capacitive sensor 20 to a material having a different dielectric constant will necessarily change the capacitance of the sensor 20. Since changes in the concentration of water in the emulsion changes the dielectric constant of that material, the capacitance of the water sensor 20 varies with the water concentration present in the emulsion disposed between the plates 22.

In order to monitor such changes in the capacitance of the sensor 20, the apparatus 10 is provided with a frequency oscillator 40. The oscillation frequency of the frequency oscillator 40 changes in direct relation to the capacitance of the sensor 20, and the oscillator 40 produces an oscillating signal having a frequency which is inversely proportional to the capacitance of the sensor.

As shown in FIG. 1, the oscillating signal output by oscillator 40 is preferably encoded as a differential signal via a RS-422 driver 46. The differential signal is then transmitted via a standard twisted pair cable to a RS-422 receiver 47. Receiver 47 decodes the differential signal and forwards the decoded signal to a frequency to voltage converter 60. As its name suggests, the frequency to voltage converter 60 develops an output voltage proportional to the frequency of the oscillating signal received from the oscillator 40. In the preferred embodiment, the ratio between the input and the output of the frequency to voltage converter 60 is 20 KHz/volt.

In any event, as shown in FIG. 1 the output voltage of the converter 60 is passed through a conventional low pass filter 70 to remove any high frequency noise generated by the sensor 20 or developed in transmission line 50. The filtered signal is then digitized by a conventional analog to digital converter 80 and converted to a water concentration value by a water concentration converter 82 whose output can be used to control the mixer. In other words, the water sensor 20, oscillator 40, RS-422 device 46, cable 50, RS-422 receiver 47, frequency to voltage converter 60, filter 70, analog to digital converter 80, and water concentration converter 82 can be coupled to the mixer to form a feedback loop to regulate the water concentration in the monitored emulsion.

The manner in which the mixer adjusts the water levels of the emulsion when such a feedback loop is employed is not relevant to the instant invention and will not be further described here. Suffice it to say that any conventional mixer can be used to this end without departing from the scope of the invention. For example, the mixer could add water or ink to the emulsion in a full scale process, or the mixer could control the flow rate of any or all components of the emulsion without departing from the scope of the invention.

Figure 2:
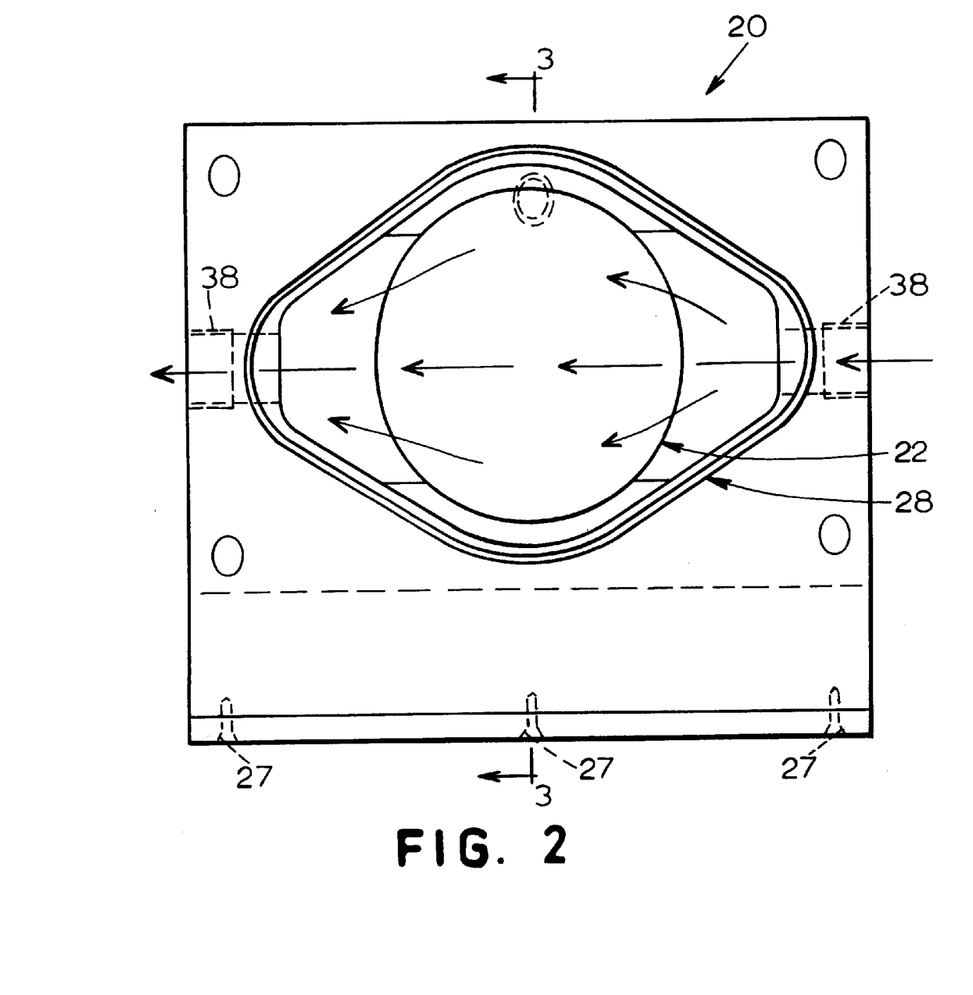
FIG. 2 is a top view of a sensor constructed in accordance with the teachings of the instant application.
Figure 3:
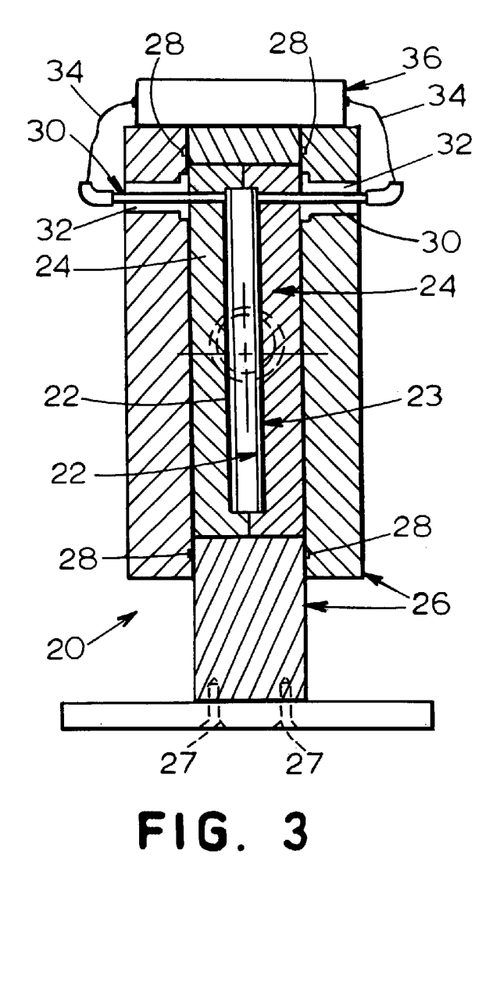
FIG. 3 is a cross-sectional view of the sensor of FIG. 2 taken along line 3—3 of FIG. 2.

FIGS. 2 and 3 provide a detailed view of a sensor 20 constructed in accordance with the teachings of the invention. As shown in these figures, the sensor 20 preferably includes a pair of metallic plates 22. Although other shapes and dimensions can likewise be employed without departing from the scope of the invention, in the preferred embodiment the plates 22 comprise a pair of parallel disks separated by a distance. Preferably, the ratio of the diameter of the disks 22 to the distance between those disks 22 falls between approximately 12:1 and approximately 20:1. The disks are preferably constructed of a metal such as stainless steel and their opposed faces are preferably coated with a plastic such as Teflon. The plastic coating is employed to provide insulation between the plates 22 and the emulsion and to prevent corrosion of the plates. The insulation is required to prevent leakage current between the plates as the emulsion will typically include conductive additives from the dampening solution.

For the purposes of locating and preventing movement of the disks 22 during use, each of the disks 22 is preferably cemented within a dielectric side shield 24. As shown in FIG. 3, the side shields 24 are complementary and define a cavity for receiving the opposed disks 22 and for maintaining a predefined distance therebetween in accordance with the above-noted ranges. Preferably, the disks 22 are cemented in place with a dielectric cement 23 such as the epoxy cement sold by Loctite, and the dielectric side shields 24 are constructed of a non-conductive material such as Delrin.

In order to shield the disks 22 from stray electromagnetic fields and the like, the sensor 20 is preferable provided with a metallic housing 26. As shown in FIG. 3, the metallic housing 26 defines a cavity sized to rigidly secure the complementary dielectric side shields 24 in a fixed location. Preferably, the housing 26 is adapted to interact with fasteners 27 such as bolts or screws to provided a means for securing the sensor 20 in a suitable location. Preferably, gaskets 28 are used to seal the housing 26 against fluid leakage. As shown in FIG. 3, the housing 26 is preferably composed of two opposed side components, a top component, and a bottom component secured together in a conventional manner by bolts (not shown).

To enable monitoring capacitance changes across the disks 22, the housing 26 is further provided with two opposed apertures. These opposed apertures each receive a metallic rod 30 housed within a dielectric sleeve 32 sized to fit closely within the apertures. The metallic rods 30 are each coupled at one end to a respective one of the disks 22, and at the other to a connecting wire 34. Connecting wires 34 (shown schematically in FIG. 1) are each coupled to an oscillator box 36 containing the oscillator 40 and the RS-422 driver 46. Preferably, the oscillator box 36 is mounted upon the housing 26 as shown in FIG. 3 to minimize the length of the wires 34 thereby minimizing unwanted capacitance associated therewith.

Figure 6:
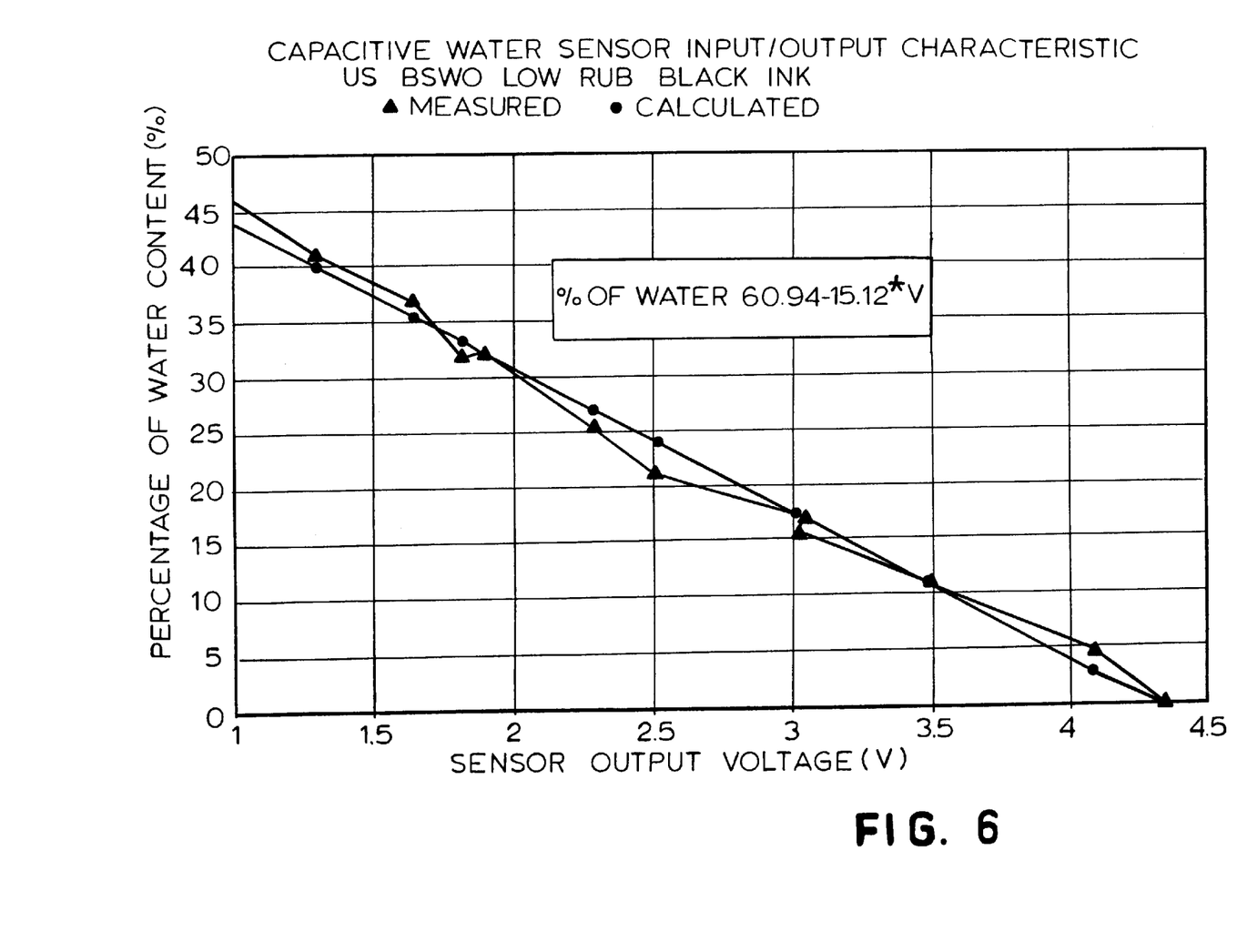
FIG. 6 is a graph illustrating exemplary output characteristics of the sensor of FIGS. 2 and 3.

As best shown in FIG. 2, the housing 26 preferably defines two opposed apertures 38 in communication with the gap defined by the disks 22. These apertures 38 provide means for pumping the water-ink emulsion between the opposed disks 22. As explained above, changes in the dielectric constant of that emulsion will produce corresponding changes in the capacitance of the sensor 20. As a result, the output of the frequency to voltage converter 60 is linearly proportional to the water concentration of consistently blended water-ink emulsions having water concentrations between approximately 0 and 50%. This linear relationship obviates the need for the logarithmic amplifiers employed in prior art devices. As shown in FIG. 6, a sensor 20 constructed in the above manner achieves such a linear relation over the desired range.

Figure 4:
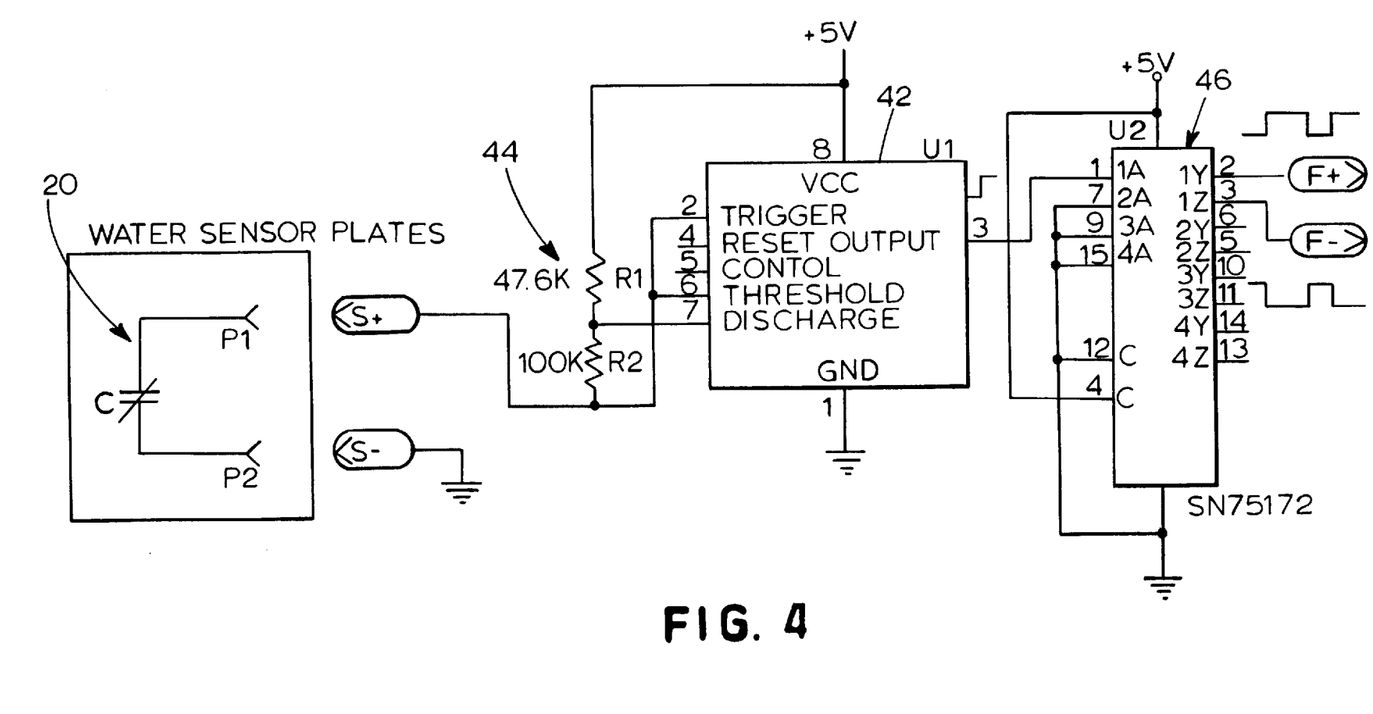
FIG. 4 is a circuit diagram of the driver electronics employed in the preferred embodiment of the apparatus of FIG. 1.
Figure 5:
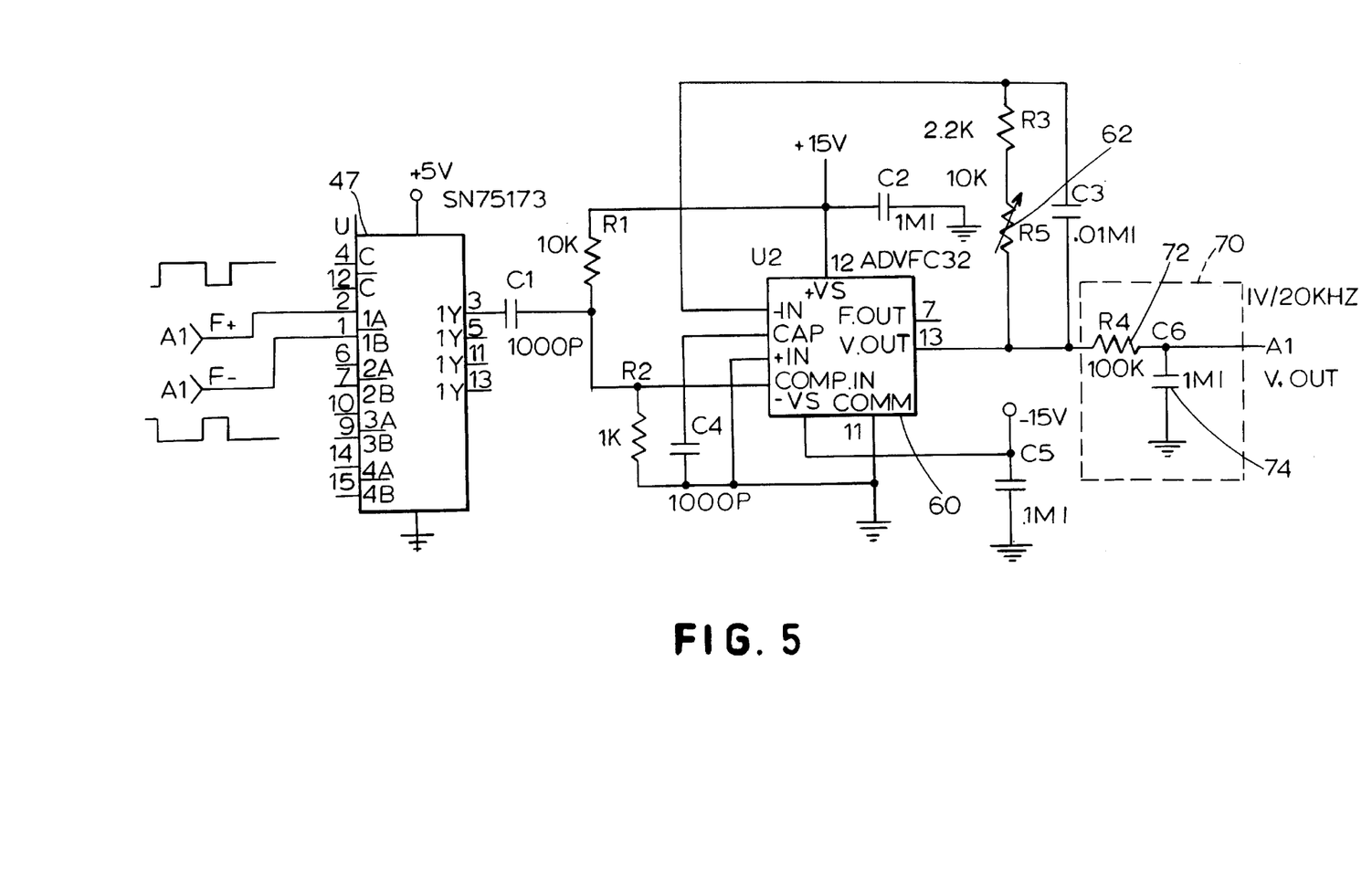
FIG. 5 is a circuit diagram of the receiver electronics employed in the preferred embodiment of the apparatus of FIG. 1.

Exemplary circuits for implementing the frequency oscillator 40, RS-422 driver 46, cable connection 50, RS-422 converter 47, frequency to voltage converter 60 and low pass filter 70 are shown in FIGS. 4 and 5. Persons of ordinary skill in the art will readily appreciate, however, that numerous modifications to these circuits can be implemented without departing from the scope of the invention.

As shown in FIG. 4, the frequency oscillator 40 is preferably implemented by a conventional '555 timer 42 with suitable biasing circuitry in the form of a voltage divider network 44. Timer 42 acts as a multi-vibrator with divider network 44 and capacitive sensor 20 forming an RC-circuit defining the time constant therefor. More specifically, the timer 42, divider network 44, and capacitive sensor 20 are coupled to a 5 volt supply as shown in FIG. 4. When power is initially applied, the capacitive sensor will charge in a known manner. When the sensor 20 charges to a predetermined level, timer 42 will output a pulse and sensor 20 will be discharged. This process will continue to cycle between charging and discharging of the sensor 20 such that timer 42 outputs an oscillating signal having a frequency defined by the time constant of the RC circuit.

Since the resistance of the divider network 44 is constant, the time constant of the RC circuit is dependent upon the capacitance of sensor 20. Therefore, changes to the capacitance of sensor 20 caused by changes in the dielectric constant of the emulsion between the plates 22 will change the time constant of the RC circuit and, thus, the output frequency of timer 42. In the preferred embodiment, the output frequency of timer 42 is defined by the equation:

$$F = \frac{1.44}{(R_1 + 2R_2)C}.$$

F is the output frequency in Hertz: $R_1$ and $R_2$ are the resistances of the resistors in the divider network 44; and C is the capacitance of sensor 20 in farads.

Preferably, the output of the timer 42 has a frequency range of approximately 0–100 KHz. To this end, the sensor 20 is preferably constructed, and the consistently blended water-ink emulsion is preferably selected, such that the sensor 20 has a nominal working capacitance of 150–350 pf. Also to this end, the resistors of the divider network 44 are preferably selected to have resistances of 47.6 K ohms and 100 K ohms. When so constructed sensor 20 and divider network 44 should establish an RC time constant that places the output of timer 42 within the desired 0–100 KHz range for all expected water concentrations.

To couple the output of the timer 42 to the frequency to voltage converter 60 with minimal interference and signal loss, a conventional twisted pair cable 50 with support circuitry in the form of RS-422 driver 46 and RS-422 receiver 47 is provided as shown in FIGS. 4 and 5. In the preferred embodiment, the RS-422 driver 46 receives the output of the timer 42 and converts it into two equal signals having the same frequency as the output of the timer. As shown in FIG. 4, the paired signals are out of phase by 180 degrees. The paired signals developed by RS-422 driver 46 are transmitted via cable 50 to RS-422 receiver 47. Receiver 47 reconstitutes a single signal from the paired signals which is substantially the same as the output of timer 42. In the preferred embodiment, driver 46 and receiver 47 are respectively implemented by commercially available chips sold by Texas Instruments as part Nos. SN75172 and SN75173, although other circuits might likewise be appropriate.

As shown in FIG. 5, in the preferred embodiment, the reconstituted output of the timer 42 is converted by a conventional frequency to voltage converter 60 to a signal having a voltage proportional to the frequency of the timer output. As discussed above, the timer 42 preferably has an output range of 0–100 KHz. As also mentioned above, the ratio between the input and output of the frequency to voltage converter 60 is preferably 20 KHz/volt. This preferred frequency range and ratio ensures converter 60 has an output voltage between 0 and 5 volts, which can easily be processed by a downstream analog to digital converter 80. Preferably, converter 60 comprises a converter sold by Analog Devices as part No. ADVFC32, but other converters could also be implemented in this role without departing from the scope of the invention.

The frequency to voltage converter 60 is biased into a proper operating range by conventional biasing circuitry, as shown in FIG. 5. As also depicted in FIG. 5, the bias circuitry is preferably provided with means for calibrating the converter 60 in the form of a variable resistance 62.

As mentioned above in connection with FIG. 1, the output of the converter 60 is preferably passed through a low pass filter 70 before being digitized by an analog to digital converter 80 and converted to a water concentration value by water concentration converter 82. As shown in FIG. 5, the low pass filter 70 is preferably implemented by resistor 72 and capacitor 74 in a conventional manner.

In the preferred embodiment, the water concentration converter 82 is implemented by a microprocessor programmed in a conventional manner to perform the linear mapping function shown in FIG. 6. The mapping function is linear for water concentrations between 0 and 50% in consistently blended emulsions. The mapping function is defined by the equation:

Water Concentration $= X - Y * V$.

X and Y are constants and V is the output voltage of the frequency to voltage converter 60. The values of constants X and Y are dependent upon the additives and ink formulations employed in the emulsion as well as the degree of blending therebetween. The constants X and Y can be determined by empirical methods such as well known regression techniques. As shown in FIG. 6, in one example, X=60.94 and Y=15.12 for a black ink sold by U.S. Ink in a consistently blended emulsion.

As also shown in FIG. 6, the mapping function typically has a negative slope where, as water concentration increases, the output of the frequency to voltage converter 60 decreases.

Those skilled in the art will readily appreciate that, although in the preferred embodiment, water concentration converter 82 is implemented by a programmed microprocessor, other approaches can be used without departing from the scope of the invention. For example, a voltage divider network or other hard wired arithmetic circuit could be implemented in this role. Similarly, although in the preferred embodiment, an analog to digital converter 80 is used to digitize the output of converter 60, persons of ordinary skill in the art will appreciate that, if desired, the analog to digital converter 80 could be eliminated and the output of converter 60 could be processed by an analog water concentration converter 82 without departing from the scope of the invention.

As mentioned above, in the preferred embodiments, a consistently blended ink-water emulsion is employed. A new and improved mixer for producing such uniform blending will now be described. The mixer is disclosed and claimed in co-pending U.S. Pat. No. 08/927,200.

Figure 7:
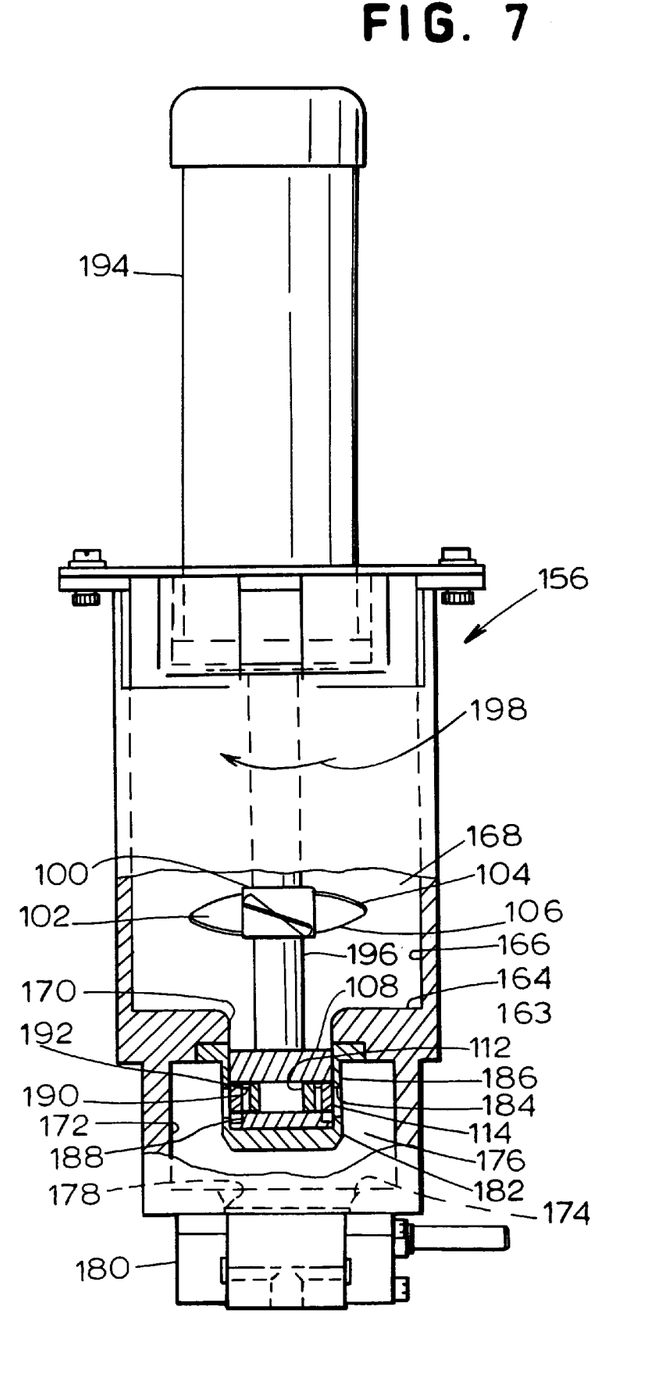
FIG. 7 is a side elevational view, partially in cross-section, of a liquid mixing and dispersing apparatus.
Figure 9:
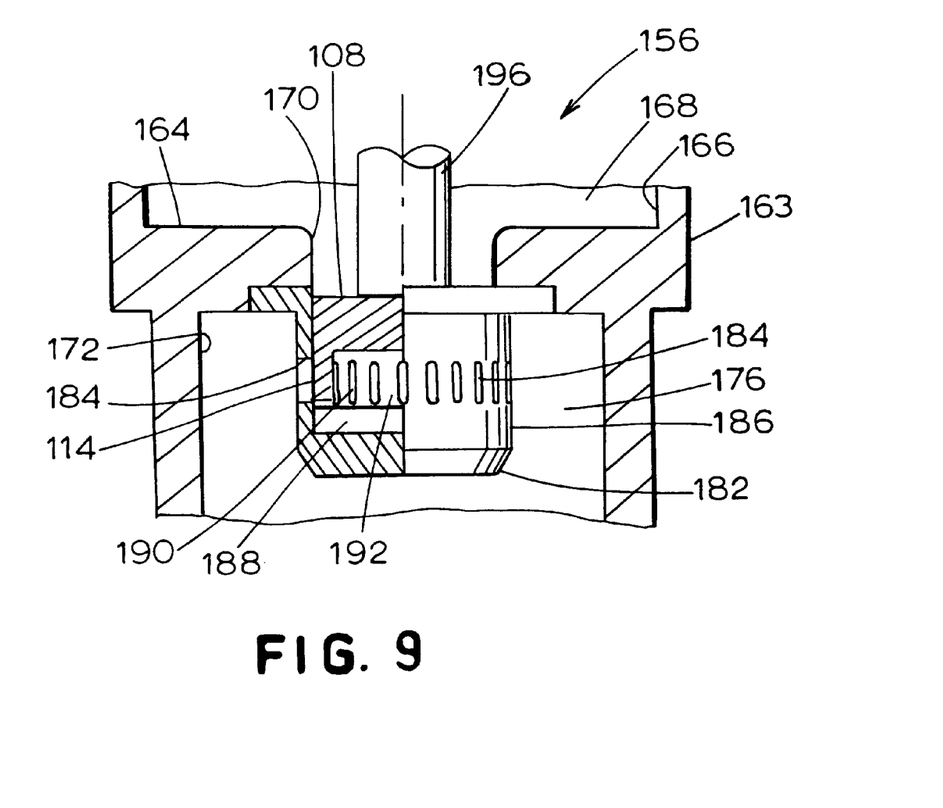
FIG. 9 is a fragmentary side elevational view of the rotor, the inner stator member, and the outer stator member taken generally along lines 9—9 of FIG. 8.

With reference to FIGS. 7 and 9, the mixing and dispersing apparatus 156 includes a vessel 163 comprising a first circular horizontal wall 164, and a cylindrically-shaped upper vertical wall 166 having a height of about 21.0 cm and an inner diameter of about 17.8 cm, that together define a cylindrically-shaped upper chamber 168.

The first horizontal wall 164 has a circular opening 170 therein having a diameter of about 6.4 cm. The vessel 163 also includes a cylindrically-shaped lower vertical wall 172 having an inner diameter of about 13.8 cm, that is disposed directly below the first horizontal wall 164. The first horizontal wall 164, the cylindrically-shaped lower vertical wall 172, and a second circular horizontal wall 174, together define a cylindrically-shaped lower chamber 176. The second circular horizontal wall 174 has a substantially square-shaped opening 178 therein, having dimensions of about 8.0 by 8.0 cm, that leads to a gear pump 180, driven by a gear pump motor (not shown), that pumps the water-ink emulsion ink out of the lower chamber 176.

A cup-shaped outer stator 182 is fixedly attached to the first horizontal wall 164 and is perforated by twenty four vertical slots 184 evenly distributed about an outer stator cylindrical wall 186, having a wall thickness of about 4.8 mm. A cup-shaped inner stator 188 is fixedly attached to the outer stator 182 and is perforated by sixteen vertical slots 190 evenly distributed about an inner stator cylindrical wall 192, having a wall thickness of about 4.0 mm. Each of the slots 184 and 190 has a height of about 15.9 mm and a width of about 3.4 mm.

A high-speed electric motor 194 is disposed above the upper chamber 168 and drives a motor shaft 196 in a clockwise direction as viewed from above, as indicated by an arrow 198. A propeller 100 is mounted to the motor shaft 196 for rotation therewith and comprises three propeller blades 102 equally angularly spaced apart from one another by 120 degrees and each pitched by an angle of about 20 degrees with respect to the horizontal such that a leading edge 104 of each propeller blade 102 is above a respective trailing edge 106 of each propeller blade 102. The propeller 100 has a diameter of about 12.7 cm and is mounted to the motor shaft 196 in the upper chamber 168 at a location that is preferably between one half to one full propeller diameter above the first horizontal wall 164.

A rotor 108 (best seen in FIGS. 8 and 10) is mounted to the lower end of the motor shaft 196 for rotation therewith. The rotor 108 includes three horizontal blades 110 that are equally angularly spaced apart from one another by 120 degrees. Each blade 110 includes a downwardly extending inner tooth 112 and a downwardly extending outer tooth 114. Each inner tooth 112 is disposed radially inwardly of the inner stator wall 192 and each outer tooth 114 is disposed between the inner stator wall 192 and the outer stator wall 186. A relatively close clearance of about 0.4 mm is provided between the teeth 112, 114 and the stator walls 186, 192.

Figure 8:
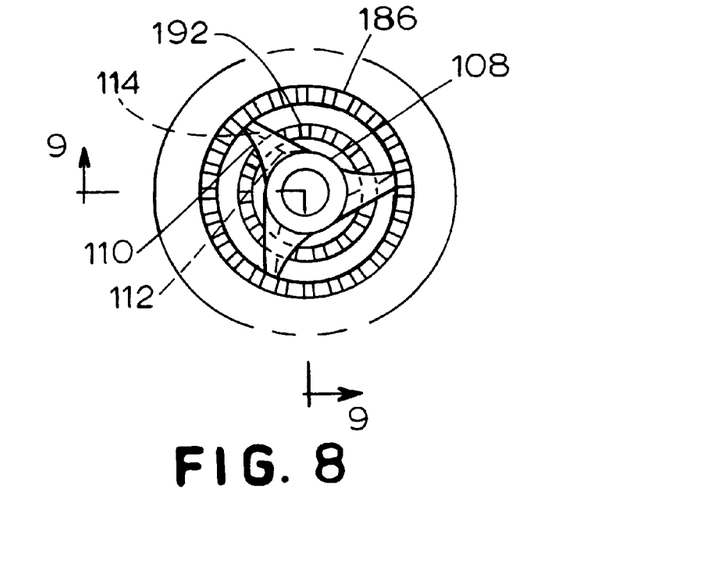
FIG. 8 is a plan view of a rotor, an inner stator member, and an outer stator member forming part of the liquid mixing and dispersing apparatus of FIG. 7.
Figure 10:
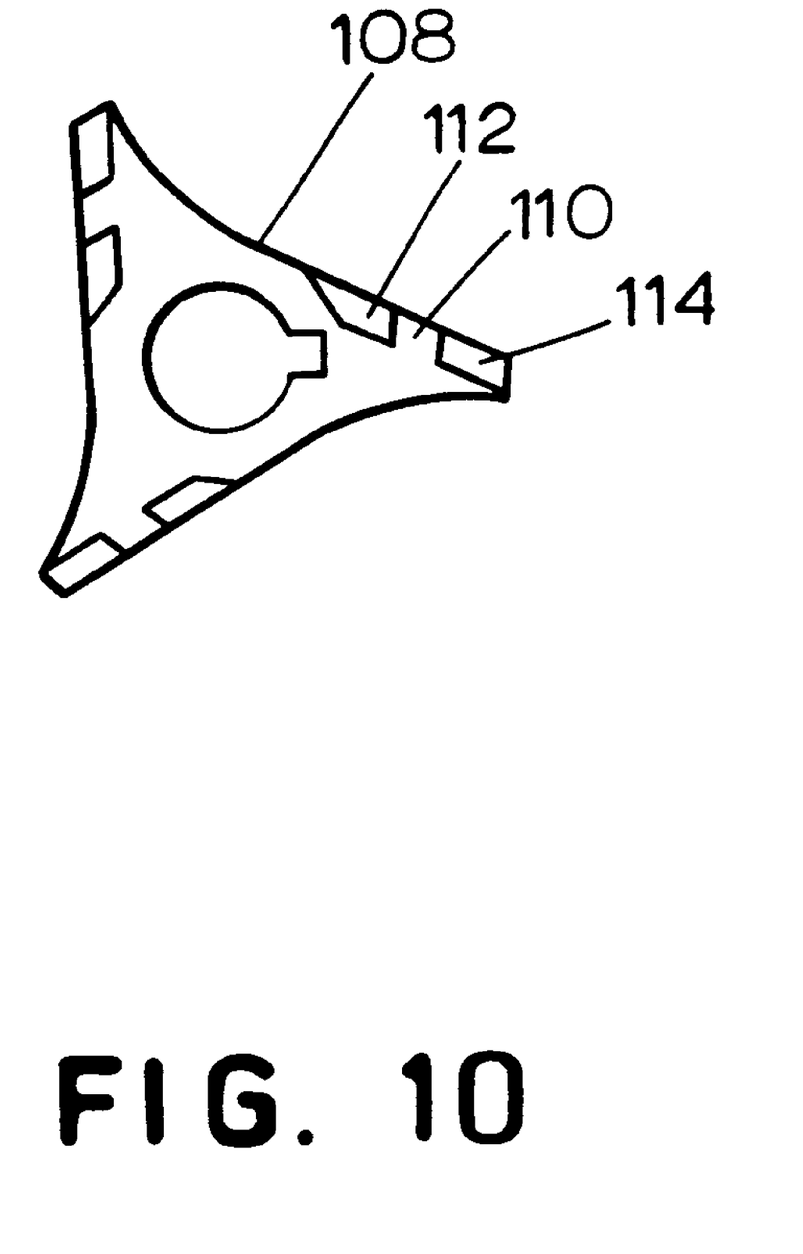
FIG. 10 is an elevational view, taken from below, showing the rotor of the apparatus of FIG. 7.

In operation, the motor 194 is rotated at a speed of between about 500 and about 4,000 revolutions per minute, and the motor shaft 196, the rotor 108, and the propeller 100 rotate at the same speed as the motor 194. Due to the pitch of the propeller blades 102, the rotation of the propeller 100 causes the ink and fountain solution in the upper chamber 168 to mix together and to flow downwardly toward the rotor 108. The rotation of the rotor 108 shears the ink and fountain solution between the rotor teeth 112, 114 and the inner and outer stator walls 192 and 186. This shearing causes the formation of a fine water-ink emulsion that is dispersed through the slots 190 and 184 in the inner and outer stator walls 192 and 186 into the lower chamber 176. The water-ink emulsion is then pumped by the gear pump 180 to a conduit for delivery to the press.

The propeller 100 pre-mixes the ink and fountain solution together and ensures that the fountain solution added to the upper chamber 168 does not simply sit on top of the ink surface and fail to mix with the ink matrix to form a water-ink emulsion having the desired water content. The propeller 100 also prevents a cavity from forming above the rotor 108, that would inhibit ink and fountain solution from flowing into the lower chamber 176.

In summary, from the foregoing, persons of ordinary skill in the art will readily appreciate that a new and improved water metering apparatus which provides a substantially linear output for water concentrations ranging between 0 and approximately 50% in a uniformly blended water-ink emulsion, and which does not employ a logarithmic amplifier has been disclosed. Significantly, the water metering apparatus can produce an output which is linearly related to water concentrations in a uniformly blended water-ink emulsion for water concentrations in the 20–50% range, namely, the normal operating range for most water-ink emulsions. In addition, persons of ordinary skill in the art will appreciate that an improved sensor for use in a water metering apparatus of the above type has also been disclosed.

Furthermore, those skilled in the art will appreciate that, although the invention has been described in connection with certain embodiments, there is no intent to limit the invention thereto. On the contrary, the intention of this application is to cover all modifications and embodiments fairly falling within the scope of the appended claims either literally or under the doctrine of equivalents.

We claim:

1. A capacitive sensor comprising:

a housing defining a first cavity;

dielectric side shields located within the first cavity, the dielectric side shields defining a second cavity; and a pair of opposed plates located within the second cavity, the plates being secured to the dielectric side shields such that the plates are spaced a distance apart, wherein the housing defines at least one aperture to permit selective location of a material to be sensed between the opposed plates, whereby capacitance of the opposed plates is related to the material between the plates.

2. A sensor as defined in claim 1 wherein the housing is metallic to shield the plates from external electromagnetic fields.

3. A sensor as defined in claim 1 wherein the plates are rigidly secured to the dielectric side shields.

4. A sensor as defined in claim 1 wherein the plates are constructed of metal, the plates have opposed faces defining the distance therebetween, and the opposed faces of the plates are coated with plastic to prevent corrosion and current leakage.

5. A sensor as defined in claim 1 further comprising a multivibrator coupled to the opposed plates.

6. A sensor as defined in claim 5 wherein the opposed plates comprise a capacitor in an R-C circuit defining an output frequency of the multivibrator.

7. A sensor as defined in claim 5 wherein the multivibrator is mounted on the housing.

8. A sensor as defined in claim 6 wherein the material comprises a uniform emulsion having a water concentration, and the output frequency of the multivibrator varies in a substantially linear manner for water concentrations above 20% and below approximately 50%.

9. A sensor as defined in claim 1 wherein the plates are substantially parallel and comprise disks having substantially the same diameter, and a ratio between the diameter of the disks and the distance therebetween is approximately between 12:1 and 20:1.

10. A water content metering apparatus for monitoring water concentration in a uniform emulsion, the apparatus comprising:

a multivibrator having an output frequency dependent upon an R-C time constant;

a capacitive sensor having a capacitance that varies in response to the water concentration of the monitored emulsion, the R-C time constant of the multivibrator varying with the capacitance of the sensor, the output frequency of the multivibrator varying in a substantially linear manner for water concentrations above 20% and below approximately 50%; and a converter coupled to the multivibrator for developing a water concentration signal in accordance with a mapping function.

11. An apparatus as defined in claim 10 wherein the mapping function has a negative slope such that, as the water concentration sensed by the sensor increases, the output frequency of the multivibrator decreases.

12. An apparatus as defined in claim 10 wherein the mapping function is substantially linear for water concentrations above 20% and below approximately 50%.

13. An apparatus as defined in claim 10 wherein the capacitive sensor comprises:

a housing defining a first cavity;

dielectric side shields located within the first cavity, the dielectric side shields defining a second cavity; and a pair of opposed plates located within the second cavity, the plates being secured to the dielectric side shields such that the plates are substantially parallel and spaced a distance apart, wherein the housing defines at least one aperture to permit selective location of the emulsion to be sensed between the opposed plates.

14. An apparatus as defined in claim 10 wherein the converter comprises a frequency to voltage converter for converting the output frequency of the multivibrator into a voltage; and a water concentration converter for executing the mapping function.

15. An apparatus as defined in claim 14 wherein the water concentration converter comprises a microprocessor.

16. An apparatus as defined in claim 15 further comprising an analog to digital converter coupled between the frequency to voltage converter and the microprocessor.

17. An apparatus as defined in claim 14 wherein the mapping function comprises:

$$\text{water concentration} = X - (Y * V),$$

wherein X and Y are constants dependent upon the emulsion and V is a voltage output by the frequency to voltage converter.

18. An apparatus as defined in claim 17 wherein X and Y are determined by a regression technique.

19. An apparatus as defined in claim 10 wherein the multivibrator is coupled to the converter by a twisted pair cable.

20. An apparatus as defined in claim 19 further comprising an RS-422 driver and an RS-422 receiver located at opposite ends of the twisted pair cable for transmitting the output frequency of the multivibrator to the converter as a differential signal.

21. An apparatus for monitoring water concentration in a uniform emulsion, the apparatus comprising:

a capacitor including two coated metallic surfaces, the two metallic surfaces being shielded from external electromagnetic fields by a metallic housing that is electrically isolated from the two metallic surfaces;

at least two aperture for pumping the uniform emulsion between the two metallic surfaces of the capacitor;

an oscillator circuit utilizing the capacitor, the oscillator circuit having an oscillation frequency depending upon the water concentration of the uniform emulsion between the two metallic surfaces; and means for converting the oscillation frequency value of the oscillator circuit into a water concentration value of the uniform emulsion using a function having a negative slope wherein as water concentration increases, the oscillating frequency decreases, the function being substantially linear for a water concentration range of above 20% and below approximately 50%.

22. An apparatus as defined in claim 21 wherein the converting means includes a frequency to voltage converter for converting a frequency signal to an analog voltage signal, an analog to digital converter for converting the analog voltage signal into a digital value, and a digital computer for determining the water concentration in the emulsion from the digital value.

23. An apparatus as defined in claim 21 wherein the converting means is located remotely from the oscillator circuit, and the oscillation frequency is sent to the converting means as a differential signal through a twisted pair cable.

* * * * *

UNITED STATES PATENT AND TRADEMARK OFFICE
CERTIFICATE OF CORRECTION

PATENT NO. : 6,169,407 B1
DATED : January 2, 2001
INVENTOR(S) : Wang et al.

It is certified that error appears in the above-identified patent and that said Letters Patent is hereby corrected as shown below:

Title page,
Under "References Cited, U.S. Patent Documents," after 5,927,200 delete "Shem-Mong" and insert -- Chou et al. --

Column 5,
Line 61, after "...the capacitive sensor," insert -- 20 --.

Column 7,
Line 42, after "...U.S. Pat. No.," delete "08/927,200" and insert -- 5,927,200 --.

Signed and Sealed this

Twenty-third Day of October, 2001

Attest:

*Attesting Officer*

NICHOLAS P. GODICI
*Acting Director of the United States Patent and Trademark Office*